(12) United States Patent
Choi et al.

(10) Patent No.: US 11,572,290 B2
(45) Date of Patent: Feb. 7, 2023

(54) FLUID TREATMENT APPARATUS

(71) Applicant: SEOUL VIOSYS CO., LTD., Gyeonggi-do (KR)

(72) Inventors: Jae Young Choi, Gyeonggi-do (KR); Kyu Won Han, Gyeonggi-do (KR); Yeo Jin Yoon, Gyeonggi-do (KR); Woong Ki Jeong, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 53 days.

(21) Appl. No.: 17/385,364

(22) Filed: Jul. 26, 2021

(65) Prior Publication Data

US 2021/0347657 A1    Nov. 11, 2021

Related U.S. Application Data

(63) Continuation of application No. 16/805,389, filed on Feb. 28, 2020, now Pat. No. 11,242,266, which is a continuation of application No. PCT/KR2018/010064, filed on Aug. 30, 2018.

(30) Foreign Application Priority Data

Aug. 31, 2017  (KR) .......................... 10-2017-0110576

(51) Int. Cl.
    C02F 1/32            (2006.01)
(52) U.S. Cl.
    CPC ................ C02F 1/325 (2013.01); C02F 1/32 (2013.01); *C02F 2201/3222* (2013.01);
    (Continued)
(58) Field of Classification Search
    CPC .. C02F 1/325; C02F 1/32; C02F 1/725; C02F 2201/3227; C02F 2201/3228;
    (Continued)

(56) References Cited

U.S. PATENT DOCUMENTS

| 9,533,896 B2 | 1/2017 | Lee et al. |
| 2010/0237254 A1 | 9/2010 | Mason et al. |
| 2020/0196589 A1* | 6/2020 | Anderson ............. A01M 19/00 |

FOREIGN PATENT DOCUMENTS

| CN | 1803643 A | 7/2006 |
| EP | 2829518 A1 | 1/2015 |

(Continued)

OTHER PUBLICATIONS

Office Action issued in corresponding CN Application 201880042488.0, dated Apr. 26, 2022, 8 pages.

(Continued)

*Primary Examiner* — Kiet T Nguyen
(74) *Attorney, Agent, or Firm* — Perkins Coie LLP (57) ABSTRACT

A sterilizing module includes a main body and a light source. The main body includes an inner surface, an outer surface and an internal space to treat a target substance in a fluid and connected an inlet and a outlet. The light source is configured to emit light toward the internal space to sterilize the target substance in the fluid. The light source includes a substrate and a plurality of light emitting structures disposed on the substrate. The plurality of light emitting structures is disposed to be spaced apart each other. A first distance between two light emitting structures is adjacent to each other varies depending on a second distance from each light emitting structure to the inner surface of the main body. The second distance has a maximum value and a minimum value of illuminance and a difference between the maximum and the minimum value thereof is about more than 75%.

11 Claims, 7 Drawing Sheets

(52) U.S. Cl.
CPC ............... *C02F 2201/3227* (2013.01); *C02F 2201/3228* (2013.01); *C02F 2303/04* (2013.01)

(58) Field of Classification Search
CPC ...... C02F 2201/3222; C02F 2201/3223; C02F 2201/3225; C02F 2303/04; C02F 2305/023; C02F 2305/10; A61L 9/20; A61L 2209/12
USPC ........................................... 250/436, 455.11
See application file for complete search history.

(56) References Cited

FOREIGN PATENT DOCUMENTS

| | | | |
|---|---|---|---|
| JP | 2014221445 | A | 11/2014 |
| JP | 6180178 | B2 | 8/2017 |
| KR | 1020080100048 | A | 11/2008 |
| KR | 1020090081660 | A | 7/2009 |
| KR | 1020090124681 | A | 12/2009 |
| KR | 1020130106993 | A | 10/2013 |
| KR | 1020160035265 | A | 3/2016 |

OTHER PUBLICATIONS

Zhang Guanghui, Research on UV Disinfection MBR Effluent and Reactor Hydraulic Characteristics and UV Dose Calculation, Mobile HowNet App, dated Jul. 13, 2022, including English Translation, 16 pages.

* cited by examiner

FLUID TREATMENT APPARATUS

CROSS-REFERENCE OF RELATED APPLICATIONS AND PRIORITY

The present application is a continuation of U.S. patent application Ser. No. 16/805,389 filed Feb. 28, 2020 which is a continuation of PCT Application No. PCT/KR2018/010064 filed Aug. 30, 2018, entitled "FLUID TREATMENT APPARATUS" which claims priorities and the benefits of Korean Patent Application No. 10-2017-0110576 filed on Aug. 31, 2017. The contents of each application noted above are incorporated by reference in their entirety.

TECHNICAL FIELD

The present disclosure relates to a fluid treatment device. More particularly, the present disclosure relates to a fluid treatment device that treats a fluid by providing a light to a fluid.

BACKGROUND

Fluids, such as water and air, contain a variety of germs or bacteria that are harmful to the health of humans, and thus, fluid treatment devices to sterilize or remove the germs or bacteria are required.

As a method for treating the fluids, there has been a method of applying ultraviolet light to the fluids. In the case of a conventionally used ultraviolet lamp, the ultraviolet lamp not only contains mercury, which is a heavy metal, but it also has a high energy consumption since an effective UV output efficiency is low compared with an actual power consumption.

With the recent development of ultraviolet LEDs, there is a need to design a module that is capable of efficiently treating fluids using ultraviolet LEDs is needed.

SUMMARY

According to one or more embodiments of the present disclosure, a sterilizing module includes a main body and a light source. The main body includes an inner surface, an outer surface and an internal space to treat a target substance in a fluid and connected an inlet and an outlet. The light source is configured to emit light toward the internal space to sterilize the target substance in the fluid. The light source includes a substrate and a plurality of light emitting structures disposed on the substrate. The plurality of light emitting structures is disposed to be spaced apart each other. A first distance between two light emitting structures is adjacent to each other varies depending on a second distance from each light emitting structure to the inner surface of the main body. The second distance has a maximum value and a minimum value of illuminance and a difference between the maximum and the minimum value thereof is about more than 75%.

In at least one variant, a ratio of the first distance to the second distance is 1:1.25 or less.

In another variant, a ratio of the first distance to the second distance is 1:0.8 to 1:1.25.

In further another variant, the difference between the maximum and the minimum value thereof is about more than 80%.

In another variant, the second distance is set at a point on the inner surface of the main body where an amount of light between the two light emitting structures reaching the point is equal to or greater than about 70% of an amount of light output from the light source.

In another variant, the first distance is set within a range that an amount of the light reaching an intermediate point between vertical points of the two light emitting structures in the normal line direction of each light emitting structure, is equal to or greater than about 70%, or about 80% of the amount of the light.

In another variant, the first distance is within a range from about 15 mm to about 30 mm.

In another variant, the light source further comprises a transparent protective portion that houses the substrate and the light source.

In another variant, the light source further comprises a base that encapsulates both sides of the protective portion.

The present disclosure provides a fluid treatment device with high fluid treatment efficiency.

Embodiments of the inventive concept provide a fluid treatment device including a pipe including an inlet and an outlet and including an internal space through which a fluid moves and a light source part disposed in the internal space and providing a light to the fluid. The light source part includes at least one light source unit including a substrate and a plurality of light sources disposed on the substrate and emitting the light. A ratio of a first distance between two light sources adjacent to each other to a second distance from each light source to an inner circumferential surface of the pipe is 1:1.25 or less when viewed in a longitudinal-section.

In one embodiment of the present disclosure, the ratio of the first distance between the two light sources adjacent to each other to the second distance from each light source to the inner circumferential surface of the pipe is 1:0.8 to 1:1.25.

In one embodiment of the present disclosure, the second distance is set from a center of the pipe to a point where an amount of light between the two light sources is equal to or greater than about 70% of an amount of light in a normal line direction of the light source when viewed in the longitudinal-section.

In one embodiment of the present disclosure, the second distance is set from the center of the pipe to a point where the amount of the light between the two light sources is equal to or greater than about 80% of the amount of the light in the normal line direction of the light source when viewed in the longitudinal-section.

In one embodiment of the present disclosure, a number of the light source units is n, and the substrates of the light source units respectively correspond to sides of a regular n-polygon when viewed in a cross-section. A number of the light source units is three or more. The first distance is within a range from about 15 mm to about 30 mm.

In one embodiment of the present disclosure, when viewed in the cross-section, the pipe has a minimum radius at a point where a ratio of an amount of light in a normal line direction of each light source unit to an amount of light on a line connecting a vertex of the regular n-polygon and a center of the regular n-polygon is about 70% or more. The minimum radius of the pipe exceeds about 10 mm.

In one embodiment of the present disclosure, each of the light source units includes three light sources.

In one embodiment of the present disclosure, the light source unit further includes a protective pipe that accommodates the substrate and the light source. The protective pipe is transparent. The light source unit further includes a base that encapsulates both sides of the protective pipe.

In one embodiment of the present disclosure, the light source has an orientation angle from about 110 degrees to about 150 degrees.

In one embodiment of the present disclosure, the inlet and the outlet are arranged substantially in parallel to a longitudinal direction of the pipe.

In one embodiment of the present disclosure, at least one of the inlet and the outlet is arranged in a direction inclined to or perpendicular to a longitudinal direction of the pipe.

In one embodiment of the present disclosure, the inlet and the outlet are arranged in a same direction when viewed in a cross-section perpendicular to a longitudinal direction of the pipe.

In one embodiment of the present disclosure, the fluid is a water.

In one embodiment of the present disclosure, the light source part emits the light in an ultraviolet light wavelength band. The light source part emits the light in a sterilization wavelength band.

Embodiments of the present disclosure provide a fluid treatment device including a pipe having an inlet, an outlet, an internal space through which a fluid moves, and a light source part disposed adjacent to the pipe and providing a light to the fluid. The light source part includes at least one light source unit including a substrate and a plurality of light sources disposed on the substrate and emitting the light. A ratio of a first distance between two light sources adjacent to each other to a second distance from each light source to an inner circumferential surface of the pipe is 1:1.25 or less when viewed in a longitudinal-section.

According to an exemplary embodiment of the present disclosure, the light source part includes first and second light source units, which face each other with the pipe interposed therebetween. Each of the first and second light source units includes a substrate and a plurality of light sources disposed on the substrate and emitting the light. A ratio of a distance between two light sources adjacent to each other in a longitudinal direction to a distance between two light sources facing each other with the pipe interposed therebetween is 1:2.5 or less when viewed in a longitudinal-section.

According to one embodiment of the present disclosure the fluid treatment device may efficiently treat a large amount of fluid uniformly and in a short time.

DESCRIPTION OF DRAWINGS

The above and other advantages of the present disclosure will become readily apparent by reference to the following detailed description when considered in conjunction with the accompanying drawings wherein.

DETAILED DESCRIPTION OF EMBODIMENTS

The present disclosure may be variously modified and realized in many different forms, and thus specific embodiments will be exemplified in the drawings and described in detail hereinbelow. However, the present disclosure should not be limited to the specific disclosed forms, and be construed to include all modifications, equivalents, or replacements included in the spirit and scope of the present disclosure.

Hereinafter, exemplary embodiments of the present disclosure will be explained in detail with reference to the accompanying drawings.

Figure 1:
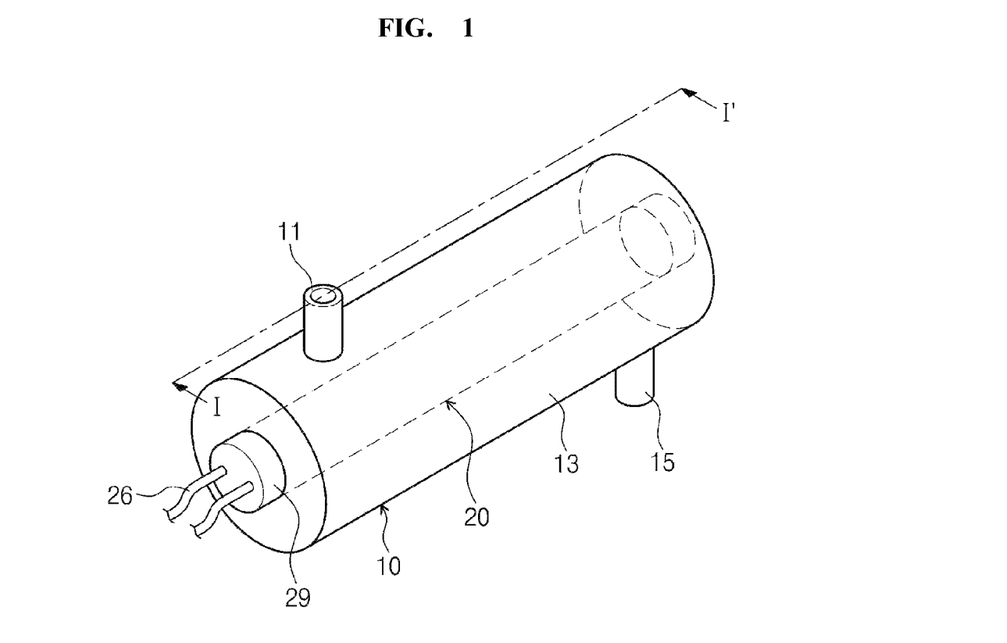
FIG. 1 is a perspective view showing a fluid treatment device according to an exemplary embodiment of the present disclosure.
Figure 2:
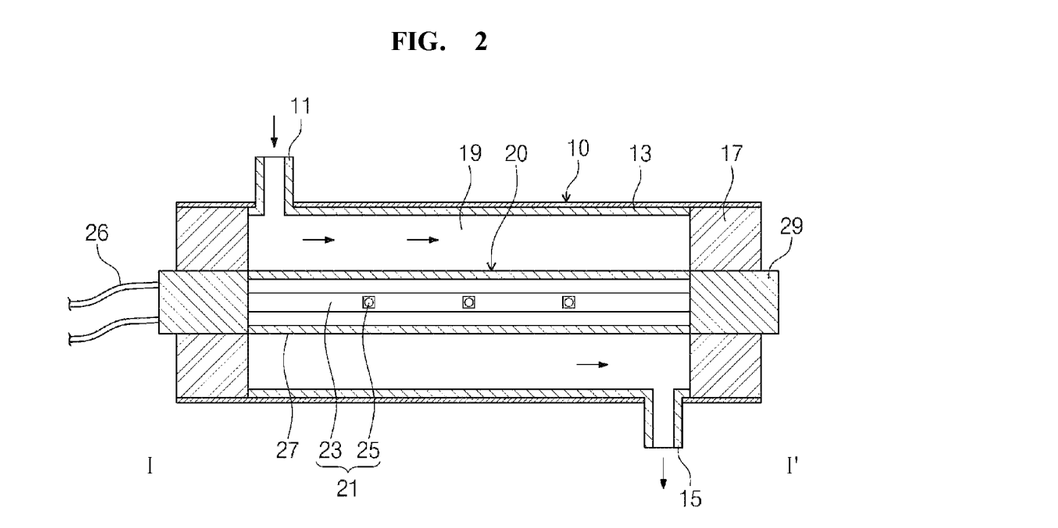
FIG. 2 is a cross-sectional view taken along a line I-I' of FIG. 1.

FIG. 1 is a perspective view showing a fluid treatment device according to an exemplary embodiment of the present disclosure, and FIG. 2 is a cross-sectional view taken along a line I-I' of FIG. 1.

The exemplary embodiment of the present disclosure relates to the fluid treatment device. In an exemplary embodiment, a fluid is a target substance to be treated using the fluid treatment device, and the fluid may be water (especially flowing water) or air. In an exemplary embodiment, treating the fluid includes, for example, sterilizing, purifying, and deodorizing the fluid using the fluid treatment device. However, in the exemplary embodiment of the present disclosure, the treatment of the fluid should not be limited thereto or thereby and may include other measures that are capable of being carried out using the fluid treatment device described later.

Referring to FIGS. 1 and 2, the fluid treatment device according to the exemplary embodiment of the present disclosure may include a pipe 10 through which the fluid flows and a light source part 20 disposed in the pipe 10 and providing a light to the fluid.

The pipe 10 may have a rod shape extending in one direction and may provide an internal space 19 in which the fluid is treated. The fluid may flow through the internal space 19. The pipe 10 may include an inlet 11 through which the fluid flows into, an outlet 15 through which the treated fluid is discharged, a main body 13 in which the fluid is treated, and a cap 17 encapsulating both sides of the main body 13.

The main body 13 may accommodate a component, for example, the light source part 20, which allows the fluid flowing into through the inlet 11 to be treated therein. The light source part 20 is described later.

The main body 13 may have a hollow pipe shape and may have a shape in which both ends in a direction in which the main body 13 extends are opened. In the exemplary embodiment of the present disclosure, the main body 13 may have a cylindrical shape. In this case, a cross section intersecting a longitudinal direction of the cylindrical shape may be a circular shape. However, the shape in cross section of the main body 13 should not be limited to the circular shape and may have a variety of shapes, such as an oval shape, a polygonal shape such as a quadrangular shape, etc.

The inlet 11 may be connected to one side of the main body 13 and connected to the internal space 19 of the main body 13. A direction in which the inlet 11 extends may be different from the extension direction of the main body 13. In the exemplary embodiment of the present disclosure, the extension direction of the inlet 11 may be inclined to or perpendicular to the extension direction of the main body 13, and thus, the fluid may move along the extension direction of the main body 13 after flowing into a direction inclined or perpendicular to the main body 13. The fluid flowing into the main body 13 through the inlet 11 is a fluid to be treated in the main body 13, for example, a target substance that is to be sterilized, purified, and deodorized.

The outlet 15 may be disposed at a position spaced apart from the inlet 11 and may be connected to the main body 13. In the exemplary embodiment of the present disclosure, a direction in which the outlet 15 extends may be inclined to or perpendicular to the extension direction of the main body 13, and thus, the fluid may be discharged in a direction inclined to or perpendicular to the main body 13 while moving along the extension direction of the main body 13. The fluid discharged from the main body 13 through the outlet 15 is a fluid that is already treated in the main body 13, for example, the target substance that is already sterilized, purified, and deodorized.

The inlet 11 and the outlet 15 may have a circular shape or an oval shape when viewed in a cross-section, however, they should not be limited thereto or thereby. The inlet 11 and the outlet 15 may have a variety of shapes, for example, a polygonal shape. In the present exemplary embodiment, the cross-section of the inlet 11 and the outlet 15 may be a cross-section in a direction crossing the extension direction of the inlet 11 or a direction in which a flow path is formed.

In the exemplary embodiment of the present disclosure, a reflective layer may be disposed on an inner circumferential surface of the pipe 10, particularly, an inner circumferential surface of the main body 13, to effectively reflect the light from the light source part 20 described later.

The reflective layer may allow the light from the light source part 20 to continuously travel inside the main body 13 without leaking to the outside. A material for the reflective layer should not be particularly limited as long as the reflective layer reflects the light. In addition, an area where the reflective layer is disposed should not be particularly limited as long as the light from the light source part 20 reaches the area, and the reflective layer may be disposed on the entire area or only in some areas of an inner surface of the pipe 10.

Although not shown in figures, a separate pipe may be further disposed at the inlet 11 and/or the outlet 15. The separate pipe may be connected to the inlet 11 and the outlet 15 by a nozzle. The nozzle may be coupled with the inlet 11 and/or outlet 15 in various ways, for example, by screw coupling(s).

The cap 17 encapsulates both ends of the main body 13 and may be disposed at the both ends of the main body 13. In the exemplary embodiment of the present disclosure, the cap 17 may include an engaging portion engaged with the main body 13. The engaging portion may be provided in a variety of shapes. For example, the cap 17 may include an insertion portion as the engaging portion, which has a diameter corresponding to an inner diameter of the main body 13, and may be inserted into and engaged with an end of the main body 13, and thus, the cap 17 may encapsulate the main body 13. Alternatively, according to another exemplary embodiment of the present disclosure, the cap 17 may include a cover portion as the engaging portion, which surrounds the end of main body 13, and the end of the main body 13 may be inserted into the cover portion, thereby encapsulating the both ends of the main body 13.

As the cap 17 encapsulates the both ends of the main body 13, the fluid flowing inside the main body 13 may be prevented from leaking to the outside. The cap 17 may include an elastic material having flexibility. A silicone resin may be used as the elastic material of the cap 17; however, the elastic material should not be limited to the silicone resin. That is, the cap 17 may be formed of another material as long as the cap 17 may stably encapsulate the both ends of the main body 13. For example, a natural rubber or a synthetic rubber may be used as the elastic material, and other polymer organic elastic materials may be used.

A through hole may be defined through the cap 17, and the light source part 20 may be inserted into the main body 13 through the through hole. In this case, both ends of the light source part 20 may protrude to one outside of both caps 17.

In the exemplary embodiment of the present disclosure, the pipe 10 may form an exterior of the fluid treatment device. However, a separate housing or additional component may be disposed outside the pipe to cover the pipe 10 according to embodiments, and in this case, the housing or the additional component may form the exterior.

In addition, in the exemplary embodiment of the present disclosure, the shape of the pipe 10 is described as extending in the one direction. However, the shape of the pipe 10 may be formed differently and may have another shape as long as the pipe 10 provides the internal space 19 through which the fluid moves and has a configuration in which the fluid is treated.

The light source part 20 may be disposed in the internal space 19 of the pipe 10 and may emit the light. In the exemplary embodiment of the present disclosure, a light source 25 may be disposed in the main body 13, i.e., in the internal space 19 of the main body 13 of the pipe 10.

The light emitted from the light source part 20 may have various wavelength bands. The light emitted from the light source part 20 may be a light in a visible light wavelength band, an infrared light wavelength band, or other wavelength bands. In the exemplary embodiment of the present disclosure, the light emitted from the light source part 20 may have various wavelength bands depending on a type of fluid and an object (e.g., germs or bacteria) to be treated, and particularly, when the fluid is sterilized, the light may have a sterilization wavelength band. For example, the light source part 20 may emit the light in the ultraviolet light wavelength band. In the exemplary embodiment of the present disclosure, the light source part 20 may emit a light having a wavelength band of about 100 nm to about 405 nm, which is a wavelength band capable of sterilizing microorganisms. In the exemplary embodiment of the present disclosure, the light source part 20 may emit a light having a wavelength band of about 100 nm to about 280 nm, may emit a light having a wavelength band of about 180 nm to about 280 nm in another exemplary embodiment, and may emit a light having a wavelength band of about 250 nm to about 260 nm in another exemplary embodiment. Since the ultraviolet light having the wavelength band has a great bactericidal power, when the ultraviolet light is irradiated at an intensity of 100 μN per 1 cm$^2$, bacteria, such as *Escherichia coli*, diphtheria bacteria, and dysentery bacteria, may be killed up to 99%. In addition, the ultraviolet light in the wavelength band may kill bacteria causing food poisoning, and thus, bacteria, such as pathogenic *Escherichia coli* causing food poisoning, *Staphylococcus aureus, Salmonella Weltevreden, S. Typhumurium, Enterococcus faecalis, Bacillus cereus, Pseudomonas aeruginosa, Vibrio parahaemolyticus, Listeria monocytogenes, Yersinia enterocolitica, Clostridium perfringens, Clostridium botulinum, Campylobacter jejuni*, or *Enterobacter sakazakii*, may be killed.

The light source part 20 may include at least one light source 25 emitting the light to emit the above-described light. The light source 25 should not be particularly limited as long as the light source 25 emits a light in a wavelength band that reacts with a photocatalyst material. For example, in the case where the light source part 20 emits the light in the ultraviolet light wavelength band, various light sources 25 emitting the ultraviolet light may be used. A light emitting diode device may be used as a representative example of the light source 25 emitting the ultraviolet light. In a case where the light source part 20 emits a light in a wavelength band other than the ultraviolet light, other known light sources 25 may be used.

When a light emitting element is used as the light source 25 of the light source part 20, the light source 25 may be mounted on a substrate 23. The substrate 23 and the at least one light source 25 may form a light source unit 21.

Figure 3:
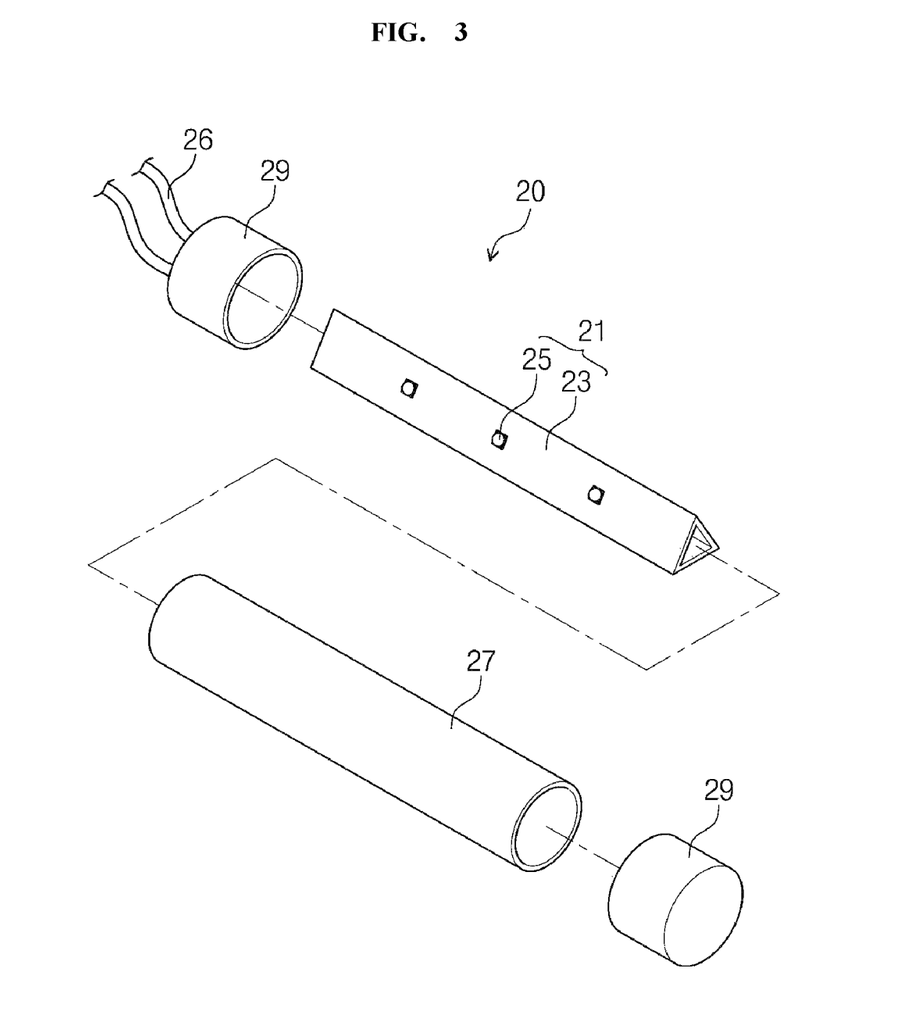
FIG. 3 is an exploded perspective view showing a light source part according to an exemplary embodiment of the present disclosure.

FIG. 3 is an exploded perspective view showing a light source part 20 according to an exemplary embodiment of the present disclosure.

Referring to FIG. 3, the light source part 20 may include the light source unit 21 having the substrate 23 and the light source 25 and a protective pipe 27 protecting the light source unit 21.

The substrate 23 may be provided to extend in a predetermined direction, for example, one direction. The light sources 25, for example, three light sources 25, may be arranged on the substrate 23 along the predetermined direction, for example, the one direction.

When the light source unit 21 includes the plural light sources 25, the light sources 25 may emit lights having substantially the same wavelength band or light having different wavelength bands from each other. For example, in the exemplary embodiment, all the light sources 25 may emit the lights in the same or similar wavelength. In another exemplary embodiment, some light sources 25 may emit lights having a portion of the ultraviolet light wavelength band, and the other light sources 25 may emit lights having the other portion of the ultraviolet light wavelength band.

In the case where the light sources 25 emit the lights having different wavelength bands, the light sources 25 may be arranged in various ways. For example, a light source emitting a light having a first wavelength band and a light source emitting a light having a second wavelength band different from the first wavelength band may be alternately arranged with each other.

The protective pipe 27 may protect the substrate 23 and the light sources 25. The protective pipe 27 may include a transparent insulating material, may protect the light sources 25 and the substrate 23, and may transmit the lights emitted from the light sources 25. The protective pipe 27 may be provided in various materials as long as the above functions are satisfied, and the material should not be limited thereto. For example, the protective pipe 27 may include a quartz or a polymer organic material. The polymer organic material may be selected by taking into account the wavelengths of the lights emitted from the light sources 25 since the wavelengths of the lights absorbed or transmitted by the polymer organic material vary depending on a type of monomer, a molding method, and molding conditions. For example, organic polymers, such as poly(methylmethacrylate) (PMMA), polyvinylalcohol (PVA), polypropylene (PP), low-density polyethylene (PE), etc., absorb very little ultraviolet light while organic polymers, such as polyester, may absorb the ultraviolet light.

The protective pipe 27 may have a long cylindrical shape along the extension direction of the substrate 23 and may be provided in a structure in which one side is opened and the other side is blocked. A base 29 may be disposed at the open side to withdraw a power wiring 26 to the outside. The base 29 may be used as a mounting member that allows the light source unit 21 to be stably placed in the protective pipe 27, and the power wiring 26 may be connected to an outer portion of the base 29 and may be connected to the substrate 23 to supply a power to the light sources 25.

In the exemplary embodiment, a photocatalyst layer including a photocatalytic material may be disposed on an inner circumferential surface and/or an outer circumferential surface of the protective pipe 27. The photocatalytic material is a material that causes a catalytic reaction by a light irradiated from the light source unit 21 and includes titanium oxide (TiO2), zinc oxide (ZnO), tin oxide (SnO2), or the like.

The photocatalyst may react to lights of various wavelength bands depending on the material therefor. In the exemplary embodiment of the present disclosure, materials that cause a photocatalytic reaction to the light in the ultraviolet light wavelength band among the lights in various wavelength bands may be used. However, the type of the photocatalyst should not be limited thereto or thereby, and another photocatalyst having the same or similar mechanism may be used depending on the light emitted from the light source unit 21. The photocatalyst may be activated by the ultraviolet light to cause a chemical reaction, and thus, the photocatalyst decomposes various pollutants or bacteria in the air in contact with the photocatalyst through a redox reaction. The air may be sterilized, purified, and deodorized by using the photocatalytic reaction. In particular, the sterilization may be a bactericidal or antimicrobial activity that destroys enzymes existing in bacteria cells and enzymes acting on a respiratory system, and thus, the growth of bacteria and fungi may be prevented and the toxins from the bacteria and fungi may also be broken down.

An area where the photocatalyst layer is disposed should not be particularly limited as long as the light emitted from the light source unit 21 may reach the area, and the photocatalyst layer may be disposed on the entire area or some areas of the inner circumferential surface and/or the outer circumferential surface of the protective pipe 27.

In the exemplary embodiment of the present disclosure, the photocatalyst layer may be disposed not only on the inner circumferential surface or the outer circumferential surface of the light source unit 21 but also on other areas to which the light reaches. For example, the photocatalyst layer may be disposed on the pipe 10, in detail, on the inner circumferential surface of the main body 13 of the pipe 10.

In the exemplary embodiment of the present disclosure, the shape of the protective pipe 27 should not be limited thereto or thereby and may have another shape. For example, the protective pipe 27 may have a shape of which both sides are opened, and in this case, the base 29 may be disposed at the both sides of the protective pipe 27. When the base 29 is disposed at the both sides, the power wiring 26 may be provided through at least one base of the bases 29 at both sides to supply the power to the light sources 25.

In the exemplary embodiment of the present disclosure, the light source part 20 may provide the light in one direction. As shown in figures, when the light sources 25 are disposed on one surface of the substrate 23, the light travels mainly in a direction substantially perpendicular to the surface on which the light sources 25 are disposed. However, the direction in which the light emitted from the light source part 20 travels may be changed in various ways.

Figure 4A:
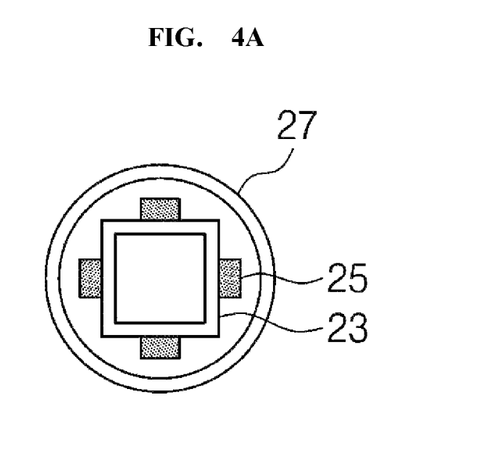
FIG. 4A is a sectional view showing light source parts according to an exemplary embodiment of the present disclosure.
Figure 4B:
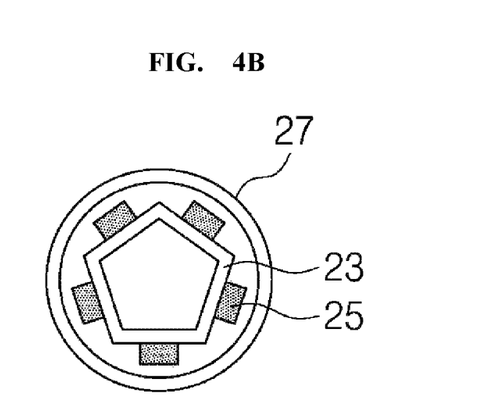
FIG. 4B is another sectional view showing light source parts according to another exemplary embodiment of the present disclosure.

FIGS. 4A and 4B are sectional views showing light source parts 20 according to an exemplary embodiment of the present disclosure.

Referring to FIGS. 4A and 4B, a light source part 20 may include at least one substrate 23 and a plurality of light sources 25 mounted on the substrate 23. The substrate 23 of a light source unit 21 may have a variety of shapes in cross-section to emit a light in various directions, e.g., as radially as possible. FIG. 3 shows the substrate 23 having the triangular shape in cross-section; however, the shape of the substrate 23 should not be limited to the triangular shape. As shown in FIGS. 4A and 4B, the substrate 23 may have a square pillar shape and a pentagonal pillar shape. For example, the shape of the substrate 23 may be provided as a regular n-polygon (n is a natural number of 3 or more). When the substrate 23 is provided as the regular n-polygon shape, uniformity of the light provided radially is the highest. In this case, the light sources 25 may be arranged on side surfaces of a triangular pillar, a square pillar, and a pentagonal pillar, and the light may exit from each side surface. As a result, the light may travel in various directions rather than one direction.

In the present exemplary embodiment, the substrate 23 may be provided as one substrate 23 having a triangular pillar shape or the square pillar shape, but it should not be limited thereto or thereby. For example, the triangular pillar-shaped, the square pillar-shaped, or the pentagonal pillar-shaped light source part 20 may be formed by assembling a plurality of light source units 21 having a flat plate shape into the triangular pillar, the square pillar, the pentagonal pillar, and the like.

In the above-described embodiments, the light source unit 21 having the straight line shape, the triangular shape, or the quadrangular shape in cross-section is shown. However, the light source unit 21 may have the circular shape or the polygonal shape according to embodiments. In addition, the regular n-polygon shape is described as a representative example in the above-described embodiment. However, the light source unit 21 may have a linear shape in cross-section by taking into account that an orientation angle of the light source 25 may be larger, the fluid may flow in various directions within the pipe 10, and the like. In this case, the light sources 25 may be disposed on both surfaces of the substrate.

MODE FOR INVENTION

The fluid treatment device having the above-described structure may efficiently treat a large amount of the fluid in a short time, which will be described below with reference to the accompanying drawings.

Figure 5:
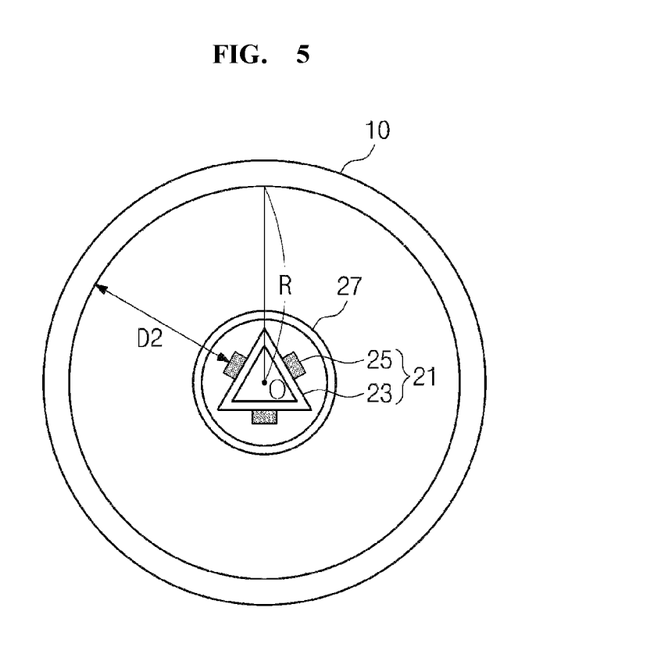
FIG. 5 is a cross-sectional view showing a fluid treatment device according to an exemplary embodiment of the present disclosure.
Figure 6:
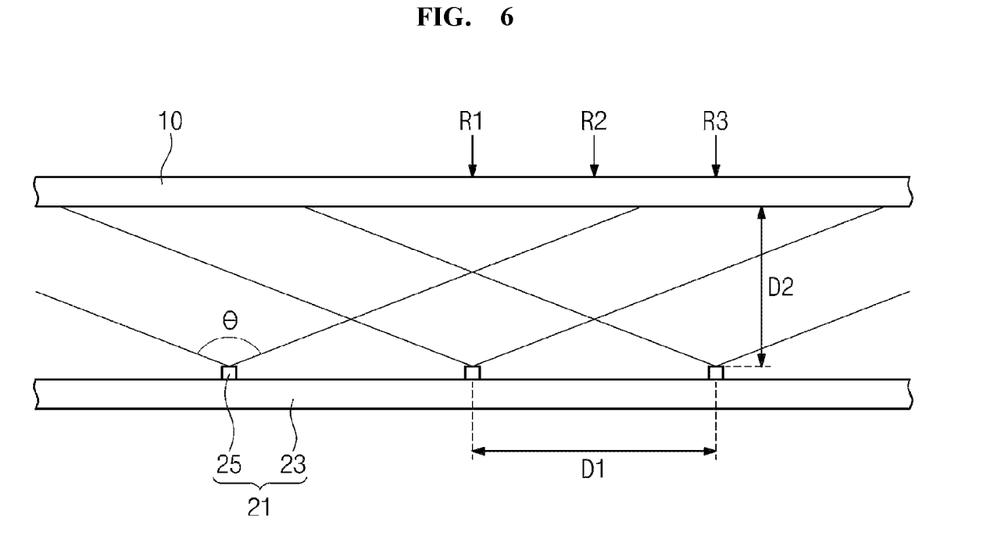
FIG. 6 is a longitudinal-sectional view showing a fluid treatment device according to an exemplary embodiment of the present disclosure.

FIG. 5 is a cross-sectional view showing a fluid treatment device according to an exemplary embodiment of the present disclosure, and FIG. 6 is a longitudinal-sectional view showing a fluid treatment device according to an exemplary embodiment of the present disclosure. For the convenience of explanation, FIG. 6 shows only the substrate 23, light sources 25, and the main body 13 of the pipe 10. Here, the cross-sectional view indicates a cross-section substantially perpendicular to a longitudinal direction of the pipe 10, and the longitudinal-sectional view indicates a cross-section taken along the longitudinal direction of the pipe 10.

In the exemplary embodiment of the present disclosure, the pipe 10 may have the cylindrical shape with a predetermined thickness and may include the inner circumferential surface and the outer circumferential surface. The protective pipe 27 of the light source part 20 may also have the cylindrical shape and may include the inner circumferential surface and the outer circumferential surface. The cross-sectional view of the pipe 10 and the protective pipe 27 are provided in the circular shape.

The substrate 23 having the triangular pillar shape and the light source 25 may be disposed in the protective pipe 27. The fluid may be filled between the outer circumferential surface of the protective pipe 27 and the inner circumferential surface of the pipe 10 and may move to the outlet 15 from the inlet 11 along the extension direction of the pipe 10.

In the exemplary embodiment of the present disclosure, centers of the triangular pillar-shaped substrate 23, the protective pipe 27, and the pipe 10 may be at the same position O when viewed in the cross-sectional view. When the center of the light source part 20 coincides with the center of the pipe 10 on the cross-sectional view, a distance R from the center O to the inner circumferential surface is constant at any position, a distance from the light sources 25 to the inner circumferential surface of the pipe 10 may also be uniform, and as a result, the light may be applied relatively uniformly to the fluid.

The fluid may be discharged to the outside after sequentially passing through the inlet 11, the main body 13, and the outlet 15. The inlet 11, the main body 13, and the outlet 15 may be sequentially arranged to facilitate the movement of the fluid. For example, the inlet 11, the main body 13, and the outlet 15 may be sequentially arranged as shown in FIG. 1, and in this case, the inlet 11 may be disposed at one side of the main body 13, and the outlet 15 may be disposed at the other side of the main body 13. Although the direction of the movement of the fluid partially varies within the body 13, the fluid generally moves along the extension direction of the pipe 10.

According to the fluid treatment device of the exemplary embodiment of the present disclosure, the light source part 20 may include a fluid treatment area in which the fluid is substantially treated. The fluid treatment area may be an area in which the light emitted by the light source part 20 reaches the fluid sufficiently so that a desired treatment is performed on the fluid, and the fluid treatment area may include an area between two light sources 25 adjacent to each other and a portion of an outer area of the light sources 25 disposed at outermost positions. For example, when m light sources 25 are sequentially provided to be spaced apart from each other by a predetermined distance (for example, when the predetermined distance is recited as "d"), the fluid treatment area may include an area ((m−1)d) between a first light source 25 to a last light source 25, an area corresponding to about ¼d as the outer area of the first light source 25, and an area corresponding to about ¼d as the outer area of the last light source 25. However, the outer areas of the first light source 25 and the last light source 25 may be set differently depending on an amount of the light from the light source 25.

According to the exemplary embodiment of the present disclosure, in the fluid treatment area, the distance between the light sources 25 and the distance from the light sources 25 to the inner circumferential surface of the pipe 10 may correspond to a predetermined range.

In the exemplary embodiment of the present disclosure, when the distance between two light sources 25 adjacent to each other is referred to as a first distance D1 and the distance from each light source 25 to the inner circumferential surface of the pipe 10 is referred to as a second distance D2 in the longitudinal-sectional view, the first distance D1 may be set in consideration of the orientation angle ($\theta$) and the light amount of each light source 25. For example, the first distance D1 may be set differently depending on the type of the light source 25 within a range from about 15 mm to about 30 mm.

In the exemplary embodiment of the present disclosure, the larger the orientation angle $\theta$ of each light source 25 is, the more efficient the fluid treatment is since the fluid treatment effect at the portion adjacent to the light source 25 and located on the side of the light source 25 may be reduced when the orientation angle ($\theta$) is small. Accordingly, it is preferable for each light source 25 to have the orientation angle $\theta$ close to about 180 degrees, and in an exemplary embodiment of the present disclosure, the orientation angle $\theta$ of each light source 25 may be about 110 degrees or more. According to another exemplary embodiment of the present disclosure, the orientation angle $\theta$ of each light source 25 may be within a range from about 110 degrees to about 150 degrees. In the present exemplary embodiment, the orientation angle $\theta$ may be an angle at which an amount of the light emitted from each light source 25 corresponds to about 50% of a maximum amount of the light emitted from each light source 25 and may mean an angle obtained by summing angles of both sides based on a line perpendicular to the center of each light source 25.

In the exemplary embodiment of the present disclosure, the first distance D1 may be set within a range in which the amount of light at an intermediate point between the two light sources 25 adjacent to each other has about 70% or more of the amount of light at a vertical point of each light source 25. According to another exemplary embodiment of the present disclosure, the first distance D1 may be set within a range in which the amount of light at an intermediate point between the two light sources 25 adjacent to each other has about 80% or more of the amount of light at a vertical point of each light source 25.

For example, when three light sources 25 are provided as shown in FIG. 6, a point perpendicular to the light source 25 positioned at a center of the light sources 25 is referred to as a first point R1, a point perpendicular to the light source 25 adjacent to one side is referred to as a third point R3, and an intermediate point between the two light sources 25 is referred to as a second point R2, the first distance D1 may be set such that the amount of light at the second point R2 is equal to or greater than about 70% or about 80% of the amount of light at the first point R1 and the third point R3. When the first distance D1 does not satisfy the above conditions, the treatment effect of the fluid may be deteriorated when the fluid passes between two adjacent light sources 25.

The second distance D2 may vary depending on the first distance D1, and a ratio of the first distance D1 to the second distance D2 may be 1:1.25 or less. When the ratio of the first distance D1 to the second distance D2 is 1.25 or less, a total cumulative amount of the light emitted from the light source 25 represents a degree to which the fluid flowing in the pipe 10 is fully treated.

When the ratio of the first distance D1 to the second distance D2 is 1.25 or more, the treatment effect on the fluid close to the inner circumferential surface of the pipe 10 may be significantly reduced since the distance between the light source part 20 and the inner circumferential surface of the pipe 10 is far.

According to the exemplary embodiment of the present disclosure, the ratio of the first distance D1 to the second distance D2 may be from 1:0.8 to 1:1.25. When the ratio of the first distance D1 to the second distance D2 is smaller than about 0.8, the distance between the light source part 20 and the inner circumferential surface of the pipe 10 is short. Therefore, the amount of the fluid flowing between the light source part 20 and the inner circumferential surface of the pipe 10 may decrease, and it may be difficult to treat a sufficient amount of the fluid depending on situations.

In the present exemplary embodiment, the light source 25 may be provided in a size smaller than that of the substrate 23, but in the drawings of the present disclosure, the size is exaggerated for convenience of description. For example, according to FIGS. 5 and 6, a distance from an upper surface of the substrate 23 to the inner circumferential surface of the pipe 10 is shown to be longer than the distance from the light source 25 to the inner circumferential surface of the pipe 10. However, since a height of the light source 25 is smaller than the height as shown and an actual difference between the distance from an upper surface of the substrate 23 to the inner circumferential surface of the pipe 10 and the distance from the light source 25 to the inner circumferential surface of the pipe 10 may be very small, it is possible to assume that the distance from the upper surface of the substrate 23 to the inner circumferential surface of the pipe 10 is the distance from the light source 25 to the inner circumferential surface of the pipe 10.

When viewed in the cross-sectional view, the pipe 10 may have a minimum radius at a point where a ratio of an amount of light in a normal line direction of each light source unit 21 to an amount of light on a line connecting the center of the regular n-polygon to a vertex of the regular n-polygon becomes about 70% or more. In the exemplary embodiment of the present disclosure, when viewed in the cross-sectional view, the substrate 23 may have the triangular pillar shape, and three light sources 25 may be provided.

As described above, in the fluid treatment device according to the exemplary embodiment of the present disclosure, the size of the pipe 10 is set such that a flow rate does not decrease while maintaining the uniformity of the light emitted from the light source 20, and thus, the fluid in the pipe 10 may be efficiently treated. Particularly, when the light emitted from the light source part 20 is the ultraviolet light having the sterilization wavelength and the fluid is water, the ultraviolet light may be evenly irradiated on the water to effectively sterilize the water, and a capacity of the sterilized water may increase.

The fluid treatment device according to an exemplary embodiment of the present disclosure should not be limited to the above-described structure, and the structure of the fluid treatment device may be changed in various ways as long as the concept of the present disclosure is maintained.

Figure 7:
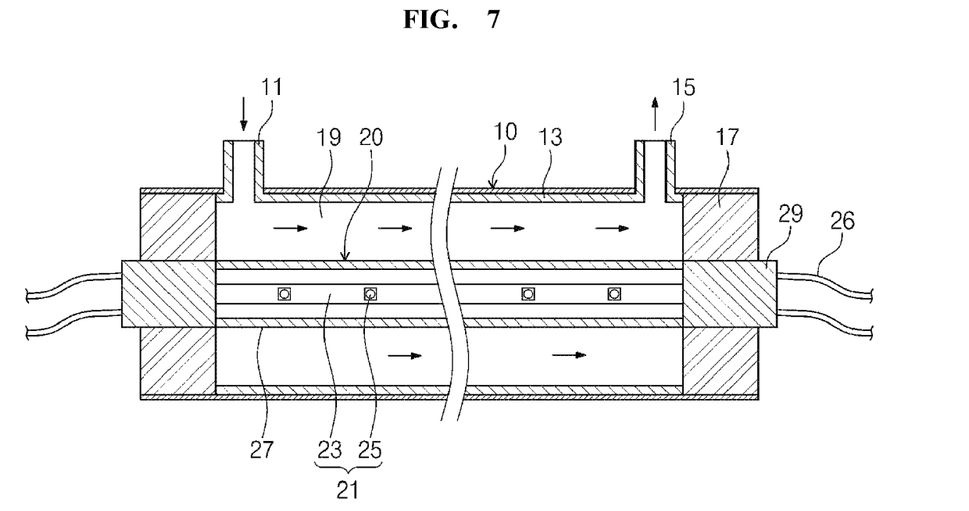
FIG. 7 is a view showing a fluid treatment device according to another exemplary embodiment of the present disclosure.

FIG. 7 is a view showing a fluid treatment device according to another exemplary embodiment of the present disclosure. Hereinafter, for the convenience of explanation, different features from those of the above-described embodiments will be mainly described.

Referring to FIG. 7, an inlet 11 and an outlet 15 of the fluid treatment device according to another exemplary embodiment of the present disclosure may be respectively connected to both sides of a main body 13 and may be arranged toward the same direction when viewed in a cross-sectional view. The inlet 11 and the outlet 15 may be connected to the main body 13 in a direction perpendicular to a direction in which the main body 13 extends, and the fluid flowing into the main body 13 through the inlet 11 may move along the extension direction of the main body 13 and may be discharged through the outlet 15. In this case, the movement direction of the fluid may correspond to a 'ㄷ'-shape, i.e., the shape of a Korean alphabet.

However, the shape of the inlet 11 and the outlet 15 should not be limited thereto or thereby. According to another exemplary embodiment of the present disclosure, the inlet 11 and the outlet 15 may be disposed in different directions from each other when viewed in a cross-sectional view.

In the present exemplary embodiment, a light source 25 may be provided in various numbers by taking into account a length of the main body 13. For example, four or more light source 25 may be provided.

Figure 8:
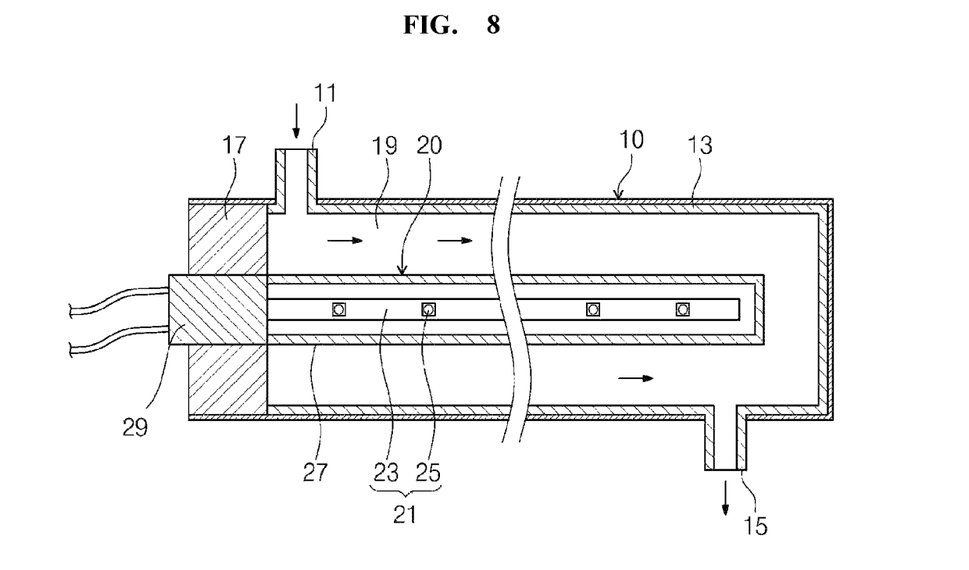
FIG. 8 is a view showing a fluid treatment device according to another exemplary embodiment of the present disclosure.

FIG. 8 is a view showing a fluid treatment device according to another exemplary embodiment of the present disclosure.

Referring to FIG. 8, a pipe 10 and a light source part 20 of the fluid treatment device according to another exemplary embodiment of the present disclosure may have different shapes from those of the above-described embodiments. In particular, the pipe 10 may have a long cylindrical shape along an extension direction and may be provided in a structure in which one side is opened and the other side is blocked. A cap 17 may be disposed at the open side of the pipe 10 to encapsulate a main body 13. A through hole through which the light source part 20 is inserted may be defined through the cap 17, and the light source part 20 may be inserted into an internal space 19 of the main body 13 through the through hole.

In the present exemplary embodiment, a light source unit 21 of the light source part 20 may have a shape corresponding to the shape of the pipe 10. In the light source part 20, a protective pipe 27 may be provided in a structure in which one side is open and the other side is blocked, and a base 29 may be disposed at the open side. A power wiring 26 from a light source 25 may be connected to the outside via the base 29.

According to the fluid treatment device of the exemplary embodiment of the present disclosure, an arrangement of each component may be partially changed as long as a ratio of a distance between two light sources 25 adjacent to each other to a distance between each light source 25 and an inner circumferential surface of the pipe 10 facing the light source 25 may be within the above-mentioned range and the fluid may be treated.

Figure 9:
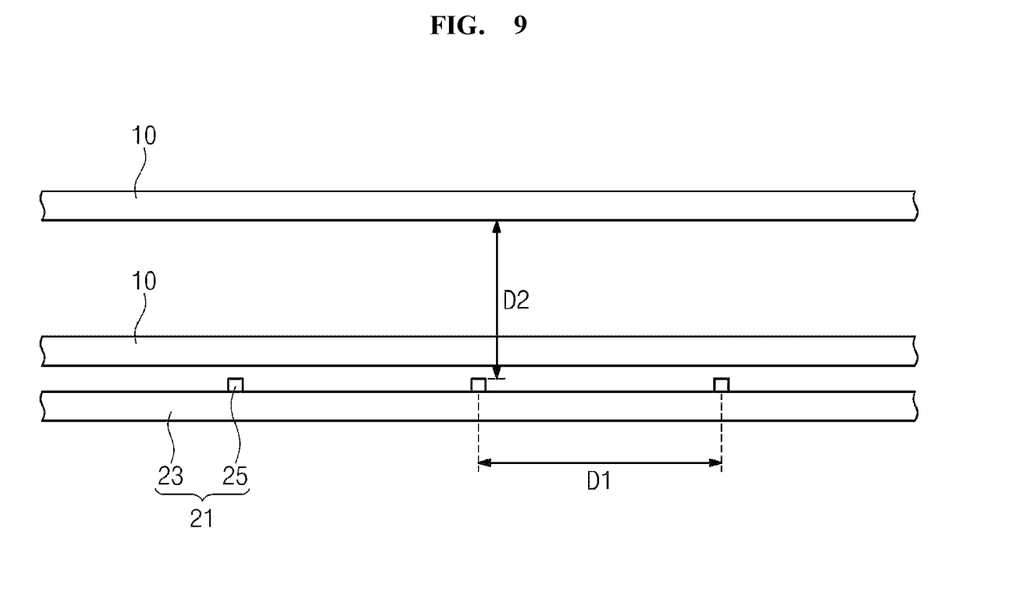
FIG. 9 is a sectional view showing an arrangement of a light source part and a pipe of a fluid treatment device according to another exemplary embodiment of the present disclosure.
Figure 10:
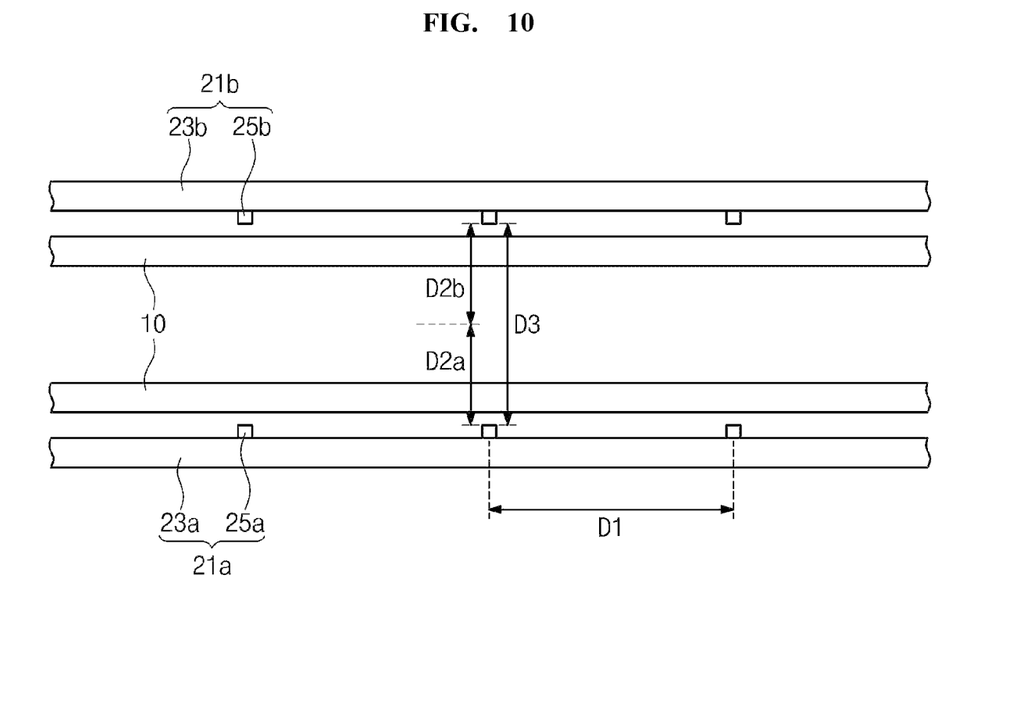
FIG. 10 is another sectional view showing an arrangement of a light source part and a pipe of a fluid treatment device according to further another exemplary embodiment of the present disclosure.

FIGS. 9 and 10 are sectional views showing an arrangement of a light source unit 21 and a pipe 10 of fluid treatment devices according to another exemplary embodiment of the present disclosure. For the convenience of explanation, FIGS. 9 and 10 show only a substrate 23 and a light source 25 of the light source unit 21 and a main body 13 of the pipe 10.

Referring to FIG. 9, the light source unit 21 may be disposed outside the pipe 10 rather than being disposed in an internal space 19 of the pipe 10. In this case, the pipe 10 may include a transparent material through which a light emitted from the light source unit 21 transmits, and a target substance to be treated may be filled in the pipe 10 and may move therein. The light emitted from the light source unit 21 may be provided to the internal space 19 of the pipe 10 and may treat the fluid filled in the internal space 19 of the pipe 10.

In this case, similar to the above-described embodiments, a ratio of a first distance D1 between two light sources 25 adjacent to each other to a second distance D2 between each light source 25 and an inner circumferential surface of the pipe 10 may be from 1:0.8 to 1:1.25 when viewed in a longitudinal-sectional view, and in this case, a large amount of the fluid in the pipe 10 may be sterilized as efficiently and uniformly as possible.

Referring to FIG. 10, the light source unit may be disposed outside the pipe 10 rather than being disposed in an internal space 19 of the pipe 10 similar to FIG. 9. However, in the present exemplary embodiment, different from FIG. 9, the light source unit may be disposed at both sides (upper and lower portions in FIG. 10) of the pipe 10. In this case, the pipe 10 may include a transparent material through which a light emitted from the light source unit transmits, and a target substance to be treated may be filled in the pipe 10 and may move therein. The light emitted from the light source unit may be provided to the internal space 19 of the pipe 10 and may treat the fluid filled in the internal space 19 of the pipe 10.

In the present exemplary embodiment, when the light source unit includes a first light source unit 21a disposed at a lower side and including a first substrate 23a and a first light source 25a and a second light source unit 21b disposed at an upper side and including a second substrate 23b and a second light source 25b, the light source unit may be disposed on both the upper side and the lower side of the pipe 10, and thus, a sufficient amount of light may reach a center of the pipe 10. When viewed in a longitudinal-sectional view, a ratio of a first distance D1 between two first light sources 25a adjacent to each other in a longitudinal direction to a second distance D2a between each first light source 25a and the center of the pipe 10 facing the first light source 25a may be 1:0.8 to 1:1.25. In addition, a ratio of a first distance D1 between two second light sources 25b adjacent to each other in the longitudinal direction to a second distance D2b between each second light source 25b and the center of the pipe 10 facing the second light source 25b may be 1:0.8 to 1:1.25. In the present exemplary embodiment, a third distance D3 may indicate a distance between the first light source 25a and the second light source 25b, which face each other with the pipe 10 interposed therebetween, and may correspond to a sum of the second distance D2a between each first light source 25a and the center of the pipe 10 facing the first light source 25a and the second distance D2b between each second light source 25b and the center of the pipe 10 facing the second light source 25b. A diameter of the pipe 10 may be determined by taking into account the third distance D3. That is, a ratio of the first distance D1 between the two adjacent first light sources 25a or between the two adjacent second light sources 25b to the third distance D3 may be from 1:1.6 to 1:2.5.

In the present exemplary embodiment, as described above, it is possible to sterilize a large amount of fluid in the pipe as efficiently and uniformly as possible.

Embodiment

Figure 11:
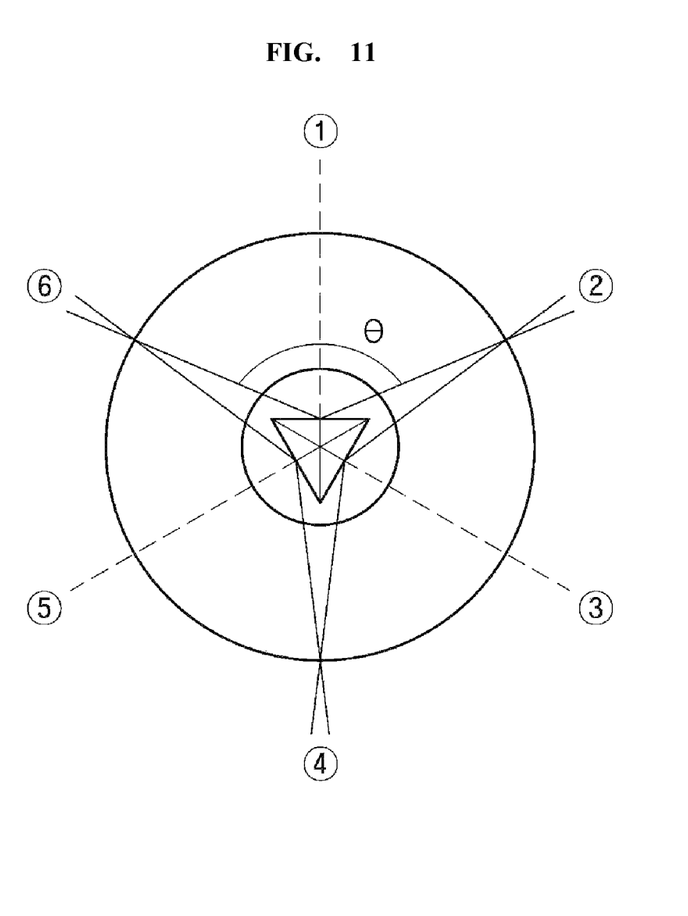
FIG. 11 is a view showing a light emission direction when viewed in a cross-sectional view.

1. Results of Illuminance Measurements in Cross-Section According to an Emission Direction of the Light Source Table 1 shows results of measuring the illuminance (μN/cm²) according to a light emission direction and a distance when the fluid treatment device according to the exemplary embodiment of the present disclosure is viewed in cross-section. FIG. 11 shows the light emission direction when viewed in cross-section and shows six directions measured in Table 1.

The distance in Table 1 corresponds to a distance between each light source and the inner circumferential surface of the main body of the pipe in the vertical direction. The illuminance of the light emitted from each light source in the vertical direction is indicated by ①, ③, and ⑤, and the illuminance of the light traveling between the light source and the light source is indicated by ②, ④, and ⑥. An optical power meter used in the present exemplary embodiment is 1918-R from Newport Corporation. The orientation angle of the light source used in the present exemplary embodiment is about 124 degrees. In Table 1 below, "AVG" denotes an average of illuminance, and "MIN-MAX" denotes a ratio of maximum to minimum values of the illuminance according to each distance. The optical power meter used in the present exemplary embodiment and the orientation angle of the light source are the same in the following embodiments, and the terminologies are also used in the same sense in the following embodiments.

TABLE 1

| Distance | ① | ② | ③ | ④ | ⑤ | ⑥ | AVG | MIN-MAX |
|---|---|---|---|---|---|---|---|---|
| 10 mm | 940 | 540 | 850 | 570 | 870 | 530 | 716.7 | 56% |
| 20 mm | 420 | 315 | 383 | 325 | 395 | 315 | 358.8 | 75% |
| 30 mm | 280 | 240 | 267 | 247 | 260 | 241 | 255.8 | 86% |
| 40 mm | 218 | 203 | 205 | 206 | 206 | 200 | 206.3 | 92% |
| 50 mm | 171 | 169 | 164 | 169 | 167 | 165 | 167.5 | 96% |

As shown in Table 1, when the distance between each light source to the inner circumferential surface of the main body of the pipe was about 10 mm, a difference between the maximum value and the minimum value of the illuminance was about 56%, and this means that the amount of the light reaching each position was significantly uneven. When the distance between each light source to the inner circumferential surface of the main body of the pipe was about 20 mm, the difference between the maximum value and the minimum value of the illuminance was about 75%, and the amount of the light reaching each position was relatively even. Thus, it is advantageous that the distance from each light source to the inner circumferential surface of the main body of the pipe exceeds about 10 mm.

2. Results of Illuminance Measurements in Longitudinal-Section According to an Emission Direction of the Light Source Table 2 shows results of measuring the illuminance according to a distance on the longitudinal-section when light emission directions are different from each other in the fluid treatment device according to the exemplary embodiment of the present disclosure. In Table 2, "direction" means the light emission directions ① and ② shown in FIG. 11. A "distance 1" in Table 2 means a distance to the outside from the light source disposed in the middle when three light sources are used and the distance between adjacent light sources is about 25 mm. That is, the distance 1 in Table 2, referring to FIG. 6, means a distance in a direction from a first point toward a third point when the first point R1 is set to zero. A "distance 2" is a distance outward from each light source.

TABLE 2

| Direction | Distance 1 Distance 2 | 0 mm | 10 mm | 20 mm | 30 mm | 40 mm | 50 mm | AVG | 0~50 mm MIN-MAX | 0~30 mm MIN-MAX |
|---|---|---|---|---|---|---|---|---|---|---|
| ① | 0 mm | 940 | 684 | 854 | 100 | 50 | 3 | 438.5 | 0% | 11% |
|   | 10 mm | 420 | 315 | 398 | 361 | 89 | 22 | 267.5 | 5% | 75% |
|   | 20 mm | 280 | 267 | 272 | 236 | 109 | 29 | 198.8 | 10% | 84% |
|   | 30 mm | 218 | 207 | 190 | 157 | 92 | 38 | 150.3 | 17% | 72% |
|   | 40 mm | 171 | 163 | 149 | 122 | 79 | 41 | 120.8 | 24% | 71% |
| ② | 0 mm | 555 | 130 | 462 | 484 | 26 | 1 | 276.3 | 0% | 27% |
|   | 10 mm | 344 | 274 | 342 | 315 | 70 | 4.5 | 224.9 | 1% | 80% |
|   | 20 mm | 236 | 232 | 229 | 194 | 93 | 26 | 168.3 | 11% | 84% |
|   | 30 mm | 199 | 198 | 179 | 148 | 85 | 39 | 141.3 | 20% | 75% |
|   | 40 mm | 160 | 158 | 142 | 119 | 78 | 43 | 116.7 | 27% | 75% |

As shown in Table 2, when viewed in longitudinal-section, the fluid treatment device according to an exemplary embodiment of the present disclosure exhibited an appropriate amount of the light when the distance 1 was about 0 mm, about 10 mm, about 20 mm, or about 30 mm. Particularly, the ratio of the maximum value to the minimum value of illuminance at the distance from 0 mm to 30 mm including the area where the light source was disposed was much higher than the ratio of the maximum value to the minimum value of illuminance at the distance from 0 mm to 50 mm including the area where the light source was not disposed. Since the illuminance was significantly reduced at 40 mm and 50 mm points corresponding to the distance 1 where the light source was not provided, it was observed that from about 0 mm to about 30 mm points correspond to the fluid treatment area. When the distance 2 was more than 10 mm in the fluid treatment area, the ratio of the maximum value to the minimum value of illuminance was more than about 75% in both ① direction and ② direction. In Table 2, when the distance 2 was equal to or greater than about 20 mm, the uniformity of the light was high. In the case of the light emitted in the ① direction and the ② direction when viewed in cross-section, the uniformity of the light was very low when the distance 2 was about 10 mm. However, when the distance 2 was about 20 mm, the uniformity of the light was relatively high.

3. Results of Sterilizing Power by Distance

Table 3 shows the results of measuring the time taken for sterilization of about 99.9% according to the distance from the light source based on one light source (3 mW, 30 mA).

TABLE 3

| Distance from light source | Time |
|---|---|
| 30 mm | 100 seconds |
| 50 mm | 5 minutes |
| 100 mm | 20 minutes |

As shown in Table 3, the sterilizing power was decreased rapidly as the distance from the light source was increased based on a single light source. In a case that the fluid to be sterilized is the flowing water, it is necessary to irradiate uniform light at the same time in the treatment area in which the flowing water is provided since an irradiation time becomes shorter.

4. Results of Illuminance Measurements According to the Shape of the Light Source Part Table 4 shows the illuminance when the light source unit of the light source part has triangular, square, and pentagonal shapes.

TABLE 4

| Direction | Triangular shape | | Square shape | | Pentagonal shape | |
|---|---|---|---|---|---|---|
| Distance | 1 | 2 | 3 | 4 | 5 | 6 |
| 10 mm | 940 | 540 | 934 | 980 | 1009 | 1099 |
| 20 mm | 420 | 315 | 400 | 530 | 420 | 544 |
| 30 mm | 280 | 240 | 256 | 389 | 289 | 389 |
| 40 mm | 218 | 203 | 196 | 299 | 229 | 308 |
| 50 mm | 171 | 169 | 159 | 241 | 184 | 249 |

Referring to Table 4, when the light source unit had the triangular shape in cross-section and the distance from each light source to the inner circumferential surface of the main body of the pipe was 10 mm, the uniformity of the light was low. However, in the case of the square shape and the pentagonal shape, the uniformity of the light was very high even when the distance from each light source to the inner circumferential surface of the main body of the pipe was 10 mm. Accordingly, it was observed that the light uniformity is improved even though the distance from each light source to the inner circumferential surface of the main body of the pipe is small when four or more light sources are used in cross-section.

5. Results 1 of Illuminance Measurements According to Interval Between Light Sources Table 5 shows the result of measuring the illuminance according to the distance on the longitudinal-section. In Table 5, a distance 2 is a distance outward from each light source. A distance 1 means a distance outward from the light source disposed in the middle when three light sources are used and a distance between adjacent light sources is 20 m. A cumulative amount in Table 5 below represents a sum of amounts of lights when the distance 1 is from 0 mm to 40 mm and the cumulative amount is measured according to the distance 2. A cumulative ratio in Table 5 shows a ratio of the cumulative amount according to the distance 2 under the assumption that the cumulative amount of the light is 100% when the distance 2 is 10 mm.

TABLE 5

| Distance 1 Distance 2 | 0 mm | 5 mm | 10 mm | 15 mm | 20 mm | 25 mm | 30 mm | 35 mm | 40 mm | 0~25 mm MIN-MAX | Cumulative amount | Cumulative ratio |
|---|---|---|---|---|---|---|---|---|---|---|---|---|
| 10 mm | 810 | 633 | 218 | 653 | 772 | 655 | 143 | 19 | 13 | 27% | 3884 | 100% |
| 15 mm | 514 | 445 | 305 | 482 | 494 | 421 | 178 | 52 | 20 | 59% | 2839 | 73% |
| 20 mm | 389 | 365 | 320 | 359 | 366 | 321 | 175 | 68 | 35 | 82% | 2295 | 59% |
| 25 mm | 317 | 309 | 287 | 299 | 288 | 277 | 157 | 93 | 48 | 87% | 1934 | 50% |
| 30 mm | 228 | 224 | 218 | 214 | 228 | 208 | 147 | 82 | 46 | 91% | 1467 | 38% |
| 35 mm | 198 | 194 | 188 | 184 | 194 | 181 | 123 | 80 | 51 | 91% | 1262 | 32% |
| 40 mm | 175 | 174 | 170 | 161 | 170 | 160 | 109 | 74 | 43 | 91% | 1119 | 29% |

In Table 4, directions 1 and 2 in the triangular shape correspond to the directions ① and ② described above, and directions 3 and 4 of the square shape indicate a direction perpendicular to the light source and a direction between two adjacent light sources, similar to the directions 1 and 2, respectively. Directions 5 and 6 of the pentagonal shape indicate the direction perpendicular to the light source and the direction between two adjacent light sources, similar to the directions 1 and 2, respectively. The distance in Table 4 is the distance from each light source to the inner circumferential surface of the main body of the pipe.

Referring to Table 5, the illuminance was significantly reduced at a point of 30 mm or more corresponding to the distance 1 where the light source was not provided, and thus, in the present exemplary embodiment, it was observed that an area from about 0 mm to about 25 mm corresponds to the fluid treatment area. In the fluid treatment area, the ratio of a maximum value to a minimum value of the illuminance was about 59% when the distance 2 was 15 mm, and the ratio of the maximum value to the minimum value of the illuminance was about 82% when the distance 2 was 20 mm. When the distance 2 was 35 mm or more, the ratio of the maximum value to the minimum value of the illuminance was about 91%, and the uniformity of the amount of the light according to the area was very high, but the overall amount of the light was decreased.

6. Results 2 of Illuminance Measurements According to Interval Between Light Sources Table 6 shows the result of measuring the illuminance according to the distance on the longitudinal-section. In Table 6, a distance 2 is a distance outward from each light source. A distance 1 means a distance outward from the light source disposed in the middle when three light sources are used and a distance between adjacent light sources is 25 m. A cumulative amount in Table 6 below represents a sum of amounts of lights when the distance 1 is from 0 mm to 40 mm and the cumulative amount is measured according to the distance 2. A cumulative ratio in Table 6 shows a ratio of the cumulative amount according to the distance 2 under the assumption that the cumulative amount of the light is 100% when the distance 2 is 10 mm.

TABLE 6

| Distance 1<br>Distance 2 | 0 mm | 5 mm | 10 mm | 15 mm | 20 mm | 25 mm | 30 mm | 35 mm | 40 mm | 0~30 mm<br>MIN-<br>MAX | Accumu-<br>lative<br>amount | Accumu-<br>lative<br>ratio |
|---|---|---|---|---|---|---|---|---|---|---|---|---|
| 10 mm | 775 | 618 | 134 | 105 | 570 | 763 | 663 | 179 | 27 | 14% | 3576 | 100% |
| 15 mm | 501 | 420 | 186 | 177 | 380 | 495 | 455 | 208 | 65 | 35% | 2822 | 79% |
| 20 mm | 370 | 320 | 290 | 285 | 350 | 339 | 279 | 175 | 33 | 75% | 2428 | 68% |
| 25 mm | 284 | 254 | 230 | 240 | 268 | 274 | 252 | 165 | 85 | 81% | 1990 | 56% |
| 30 mm | 246 | 233 | 220 | 221 | 229 | 231 | 222 | 158 | 49 | 89% | 1779 | 50% |
| 35 mm | 195 | 189 | 177 | 177 | 193 | 190 | 173 | 126 | 79 | 91% | 1420 | 40% |
| 40 mm | 181 | 177 | 165 | 165 | 171 | 180 | 165 | 110 | 80 | 91% | 1314 | 37% |

Referring to Table 6, the illuminance was significantly reduced at a point of 35 mm or more corresponding to the distance 1 where the light source was not provided, and thus, in the present exemplary embodiment, it was observed that an area from about 0 mm to about 30 mm corresponds to the fluid treatment area. In the fluid treatment area, the ratio of a maximum value to a minimum value of the illuminance was about 35% when the distance 2 was 15 mm, and the ratio of the maximum value to the minimum value of the illuminance was about 75% when the distance 2 was 20 mm. When the distance 2 was 35 mm or more, the ratio of the maximum value to the minimum value of the illuminance was about 91%, and the uniformity of the light amount according to the area was very high, but the overall amount of the light was decreased.

Although the exemplary embodiments of the present disclosure have been described, it is understood that the present disclosure should not be limited to these exemplary embodiments but various changes and modifications can be made by one ordinary skilled in the art within the spirit and scope of the present disclosure as hereinafter claimed. Therefore, the disclosed subject matter should not be limited to any single embodiment described herein, and the scope of the present inventive concept shall be determined according to the attached claims.

The invention claimed is:

1. A sterilizing module comprising:
   a main body having an inner surface, an outer surface and an internal space to treat a target substance in a fluid and connected an inlet and an outlet; and
   a light source configured to emit light toward the internal space to sterilize the target substance in the fluid;
   wherein the light source comprises a substrate and a plurality of light emitting structures disposed on the substrate, the plurality of light emitting structures is disposed to be spaced apart from each other;
   wherein a first distance between two light emitting structures adjacent to each other varies depending on a second distance from each light emitting structure to the inner surface of the main body; and
   wherein the second distance has a maximum value and a minimum value of illuminance and a difference between the maximum and minimum values thereof is about more than 75%.

2. The sterilizing module of claim 1, wherein a ratio of the first distance to the second distance is 1:1.25 or less.

3. The sterilizing module of claim 1, wherein a ratio of the first distance to the second distance is 1:0.8 to 1:1.25.

4. The sterilizing module of claim 1, wherein the difference between the maximum and minimum values thereof is about more than 80%.

5. The sterilizing module of claim 1, wherein the second distance is set at a point on the inner surface of the main body where an amount of light between the two light emitting structures reaching the point is equal to or greater than about 70% of an amount of light output from the light source.

6. The sterilizing module of claim 1, wherein the first distance is set within a range that an amount of the light reaching an intermediate point between vertical points of the two light emitting structures in a normal line direction of each light emitting structure, is equal to or greater than about 70%, or about 80% of the amount of the light.

7. The sterilizing module of claim 1, wherein the first distance is within a range from about 15 mm to about 30 mm.

8. The sterilizing module of claim 1, wherein the light source further comprises a transparent protective portion that houses the substrate and the light source.

9. The sterilizing module of claim 8, wherein the light source further comprises a base that encapsulates both sides of the protective portion.

10. The sterilizing module of claim 1, wherein the light emitting structure has an orientation angle from about 110 degrees to about 150 degrees.

11. The sterilizing module of claim 1, wherein the inlet and the outlet are arranged on a same side of the main body.

* * * * *